US005393319A

United States Patent [19]

Inaba et al.

[11] Patent Number: 5,393,319

[45] Date of Patent: Feb. 28, 1995

[54] PROCESS FOR PRODUCING OXAMIDE GRANULES

[75] Inventors: Yukio Inaba; Tomohiko Yamamoto; Genji Koga; Hideki Noguchi; Joji Funatsu, all of Ube, Japan

[73] Assignee: Ube Industries, Ltd., Yamaguchi, Japan

[21] Appl. No.: 88,804

[22] Filed: Jul. 8, 1993

[30] Foreign Application Priority Data

Jul. 10, 1992 [JP] Japan .................................. 4-223148
Aug. 21, 1992 [JP] Japan .................................. 4-264018

[51] Int. Cl.$^6$ ..................... C07C 102/06; C07C 67/36; C06G 3/00

[52] U.S. Cl. ....................................... 71/27; 71/64.03; 71/64.13; 564/135; 564/160

[58] Field of Search ....................... 71/1, 11, 27, 64.03, 71/64.13; 564/135, 160

[56] References Cited

FOREIGN PATENT DOCUMENTS 0059938 9/1982 European Pat. Off. .
0503620 9/1992 European Pat. Off. .
52-7916 1/1977 Japan .
57-160985 10/1982 Japan .
59-169527 9/1984 Japan .

OTHER PUBLICATIONS

Abstract, J59169527, Ubei Mar. 1983, "Granula oxamide . . . PUA".
Abstract, J52007916, Ubei, Aug. 1984, "Oxamide M(r . . . action".
USSR, SU-900753, Parkhomenk et al Jan. 23, 1983 "Prep of Slow-Release . . . in soil".

*Primary Examiner*—Ferris Lander
*Attorney, Agent, or Firm*—Burgess, Ryan & Wayne

[57] ABSTRACT

Oxamide granules are produced by (A) feed-mixing ammonia to a starting material comprising 60 to 100 weight % of a diester of oxalic acid with a $C_{1-6}$ aliphatic alcohol, and 0 to 40 weight % of the same aliphatic alcohol as mentioned above, to produce oxamide and the aliphatic alcohol as by-product, while controlling the aliphatic alcohol content to 5 to 40% based on the weight of the reaction mixture to provide the resultant oxamide wetted by the aliphatic alcohol; (B) granulating the wetted product while maintaining the content of the aliphatic alcohol at a level of 5 to 40% based on the weight of the wetted reaction product; (C) heat-evaporating away the aliphatic alcohol from the wetted granules; and optionally (D) re-wetting the resultant dry oxamide granules with water in an amount of 5 to 20% based on the weight of the dry oxamide granules; and (E) re-drying the re-wetted oxamide granules, to provide oxamide granules having an enhanced mechanical strength and form-stability in water.

14 Claims, 1 Drawing Sheet

PROCESS FOR PRODUCING OXAMIDE GRANULES

BACKGROUND OF THE INVENTION

1. Field of the Invention

The present invention relates to a process for producing oxamide (oxalic acid diamide) granules. More particularly, the present invention relates to a process for industrially producing oxamide granules with a high degree of purity by a series of operations including the steps of reacting an oxalic acid diester with ammonia, granulating the reaction product and drying the resultant granules within the same one apparatus.

The oxamide granules produced by the process of the present invention are practically usable as an extremely beneficial slow release fertilizer.

2. Description of the Related Arts

As a typical process for producing oxamide Japanese Unexamined Patent Publication No. 52-7,916 discloses a process comprising the steps of mixing an aliphatic alcohol with oxalic acid diester under specific conditions, then adding ammonia to the mixture to cause the oxalic acid diester to react with ammonia and produce oxamide.

In the above-mentioned process, the production of oxamide from an oxalic acid diester with ammonia is carried out in accordance with the following chemical reaction:

$$(COOR)_2+2NH_3 \rightarrow (CONH_2)_2+2ROH$$

wherein R represents a lower alkyl group having 1 to 6 carbon atoms, for example, a methyl, ethyl, propyl, butyl or pentyl group.

In the above-mentioned conventional process, the reaction of an oxalic acid diester with ammonia is carried out in a solution system containing an excessive amount of an aliphatic alcohol. This excessive amount of aliphatic alcohol exhibits an effect of restricting the production of a by-product consisting of oxalic acid monoestermonoamide during the above-mentioned reaction procedure, and therefore, the conventional process can produce oxamide with a high degree of purity at a high yield.

As mentioned above, the production of oxamide is carried out in a liquid phase reaction system which always contains an excessive amount of an aliphatic alcohol. Also, the resultant oxamide is significantly insoluble in the aliphatic alcohol. Therefore, when the oxamide-producing reaction is completed, the resultant reaction mixture is in the state of a slurry of a powdery oxamide. To obtain a high purity oxamide, it is necessary to collect the powdery oxamide from the slurry, by filtration, and remove the aliphatic alcohol contained in the collected powdery oxamide by a drying procedure at a high temperature. Namely, the conventional process for producing oxamide is disadvantageous in that the resultant oxamide must be purified by complicated refining procedures and apparatuses, and a large amount of heat energy must be consumed by these refining procedures.

In a previous invention by the inventors of the present invention, a process for producing an oxamide powder was provided. In this process, ammonia is feed-mixed to a melt of an oxalic acid diester to produce a solid mixture containing the resultant oxamide, and the resultant solid mixture is heated to evaporate-remove a by-product consisting of an aliphatic alcohol to provide an oxamide powder.

In order to use the oxamide powder as a slow action fertilizer, it is necessary to granulate the oxamide powder into a plurality of granules by using a granulating apparatus. Nevertheless, oxamide is not soluble in all the solvents including water, and thus exhibits a very poor ability to be granulated. Therefore, when oxamide is granulated by a conventional granulating apparatus as disclosed, for example, by Japanese Unexamined Patent Publication (Kokai) No. 59-169,527, it is necessary to use an expensive binder, for example, polyvinyl alcohol or to consume a large amount of energy. Otherwise a special granulating method, as shown in Japanese Unexamined Patent Publication No 57-160,985 for example, a compaction granulating method under a high pressure, which has a very poor efficiency, must be employed. Also, those conventional granulating methods and apparatuses are very complicated, and require a high processing cost and expensive equipment.

Further, there is a strong demand to provide oxamide granules having a satisfactory mechanical strength and form-stability in water, and thus easily usable as a slow action fertilizer.

SUMMARY OF THE INVENTION

An object of the present invention is to provide a process for producing oxamide granules by a reaction of an oxalic acid diester with ammonia, by a simple industrial procedure and apparatus with a saving of heat energy consumption.

Another object of the present invention is to provide a process for producing oxamide granules having a high degree of purity at a high yield.

Still another object of the present invention is to provide a process for producing oxamide granules having a high hardness and an excellent form-stability in water.

The above-mentioned objects can be attained by the process of the present invention for producing oxamide granules comprising the steps of:

(A) feed-mixing an ammonia-containing gas to a melt of a starting material comprising 60 to 100% by weight of an oxalic acid diester of the formula (I):

$$\begin{array}{l} COOR \\ | \\ COOR \end{array} \qquad (I)$$

wherein R represents a lower alkyl group having 1 to 6 carbon atoms, and 0 to 40% by weight of an aliphatic alcohol having 1 to 6 carbon atoms, to cause the oxalic acid diester to react with ammonia and produce oxamide and a by-product consisting of an aliphatic alcohol having the same alkyl group as that represented by R in the formula (I), while stirring the resultant reaction mixture and controlling the content of the aliphatic alcohol in the reaction mixture to a level of 5 to 40% by weight to provide a reaction product in the state of a wetted solid and comprising the resultant oxamide and the aliphatic alcohol;

(B) granulating the wetted reaction product into a plurality of granules; and (C) drying the resultant oxamide granules by heat-evaporating away the aliphatic alcohol therefrom, to provide dry oxamide granules.

The process of the present invention optionally further comprises the steps of (D) re-wetting the dry oxamide granules with water in an amount of 5 to 20% based on the weight of the dry oxamide granules; and (E) re-drying the re-wetted oxamide granules by, heating to provide oxamide granules having an enhanced hardness and form-stability in water.

DESCRIPTION OF THE PREFERRED EMBODIMENTS

Figure 1:
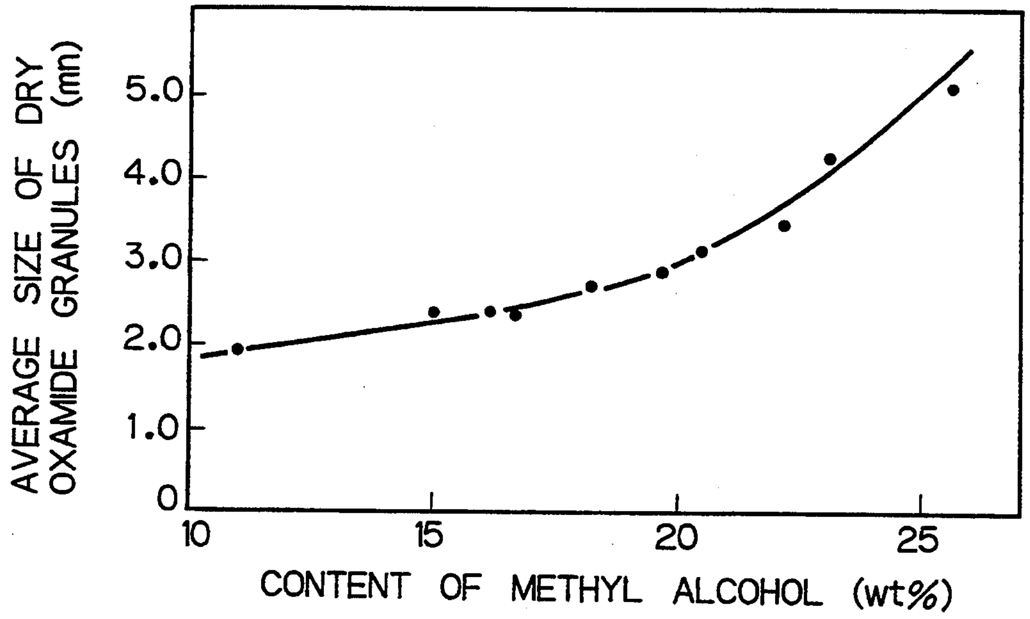
FIG. 1 is a graph showing a relationship between the content of methyl alcohol in the wetted reaction product during a granulating step and the average size of the resultant dry oxamide granules obtained in Examples 1 to 10.

The diester usable as a starting compound for the process of the present invention is selected from diesters of oxalic acid with an aliphatic alcohol having 1 to 6 carbon atoms and represented by the general. formula (I):

$$\begin{array}{l} COOR \\ | \\ COOR \end{array} \qquad (I)$$

wherein R represents an alkyl group having 1 to 6 carbon atoms.

In the process of the present invention, a starting material is prepared by mixing 60 to 100%, preferably 80 to 100%, more preferably 85 to 98% by weight of an oxalic acid diester of an aliphatic alcohol with 0 to 40%, preferably 0 to 20%, more preferably 2 to 15% by weight of the same aliphatic alcohol as mentioned above, and the resultant mixture is uniformly heated at a temperature equal to or higher than the melting point of the mixture to provide a melt of the starting material. For example, the starting material is preferably melted at a temperature of 40° C. to 160° C. The melt of the starting material is fed to the first step of the process of the present invention.

In the first step, an ammonia-containing gas is feed-mixed to the melt of the starting material, while stirring the starting material melt to start a reaction of the oxalic acid diester of the aliphatic alcohol with ammonia, in which reaction, oxamide and a by-product consisting of the aliphatic alcohol are produced.

The above-mentioned feed-mixing procedure of the ammonia-containing gas to the starting material melt is continued while controlling the content of the aliphatic alcohol contained in the reaction mixture to a level of 5 to 40%, preferably 10 to 30%, based on the total weight of the reaction mixture, whereby a reaction product comprising the resultant oxamide with a high degree of purity and the aliphatic alcohol is obtained in the state of a wetted solid. The feed-mixing procedure is preferably carried out by stirring the reaction mixture.

The ammonia-containing gases include a 100% ammonia gas and mixed gas of ammonia with an inert gas, for example, nitrogen gas, carbon dioxide gas or argon gas. Preferably, the ammonia-containing gas contains ammonia in a content of at least 50% by volume, more preferably at least 60% by volume.

The aliphatic alcohol to be mixed with the oxalic acid diester has 1 to 6 carbon atoms and is preferably selected from methyl alcohol, ethyl alcohol, n- and iso-propyl alcohols, n-, iso-, and sec- butyl- alcohol, pentyl alcohols and hexyl alcohols.

The aliphatic alcohol to be contained in the starting material is preferably the same as the aliphatic alcohol used to prepare the oxalic acid diester. Namely, the alkyl group of the aliphatic alcohol contained in the starting material is preferably the same as the alkyl group represented by R in the formula (I) for the oxalic acid diester.

Where the aliphatic alcohol in the starting material has the same alkyl group as that represented by R in the formula (I), the resultant aliphatic alcohol produced as a by-product from the reaction of the oxalic acid diester with ammonia is the same as the aliphatic alcohol contained in the starting material. In this case, a fraction of the aliphatic alcohol evaporate-removed from the reaction mixture can be easily condensed an then returned to and re-used in the preparation of the starting material.

Nevertheless, the aliphatic alcohol to be contained in the starting material may have a different alkyl group from that represented by R in the formula (I) for the oxalic acid diester, as long as the aliphatic alcohol contained in the starting material can be separated from the aliphatic alcohol produced as a by-product.

During the feed-mixing step of the process of the present invention, the composition of the reaction mixture is successively changed and the state of the reaction mixture is also successively changed from a melt (liquid) to a paste, and then to a solid wetted by the aliphatic alcohol, as of the reaction proceeds.

With respect to the change in the composition of the reaction mixture, in an initial stage, the reaction mixture contains a large amount of non-reacted oxalic acid diester. With the progress of the ammonia-addition-decomposing reaction between the oxalic acid diester with ammonia, the content of the oxalic acid diester in the reaction mixture decreases and the contents of the reaction products including oxamide and oxalic acid monoestermonoamide increases in the reaction mixture. In the final stage of the reaction, the oxalic acid monoestermonoamide is converted to oxamide by the ammonia-addition-decomposing reaction, and substantially disappears in the reaction product, and thus the resultant reaction product contains oxamide with a high degree of purity.

Also, during the feed-mixing stage, the reaction mixture is continuously stirred and the content of the aliphatic alcohol in the reaction mixture is controlled to a level of 5 to 40% based on the total weight of the reaction mixture, by evaporate-removing the resultant aliphatic alcohol.

In the process of the present invention, the continuation of the feed-mixing procedure of the ammonia-containing gas to the reaction mixture while controlling the content of the aliphatic alcohol in the reaction mixture to a level of 5 to 40% by weight is specifically important to substantially completely convert a by-product consisting of oxalic acid monoestermonoamide, which negatively affects growth of plants, to oxamide and to finally obtain oxamide with a high degree of purity.

Also, by maintaining the content of the aliphatic alcohol in the reaction mixture at a level of 5 to 40% by weight, when the reaction is completed, the resultant reaction product in the wetted solid state has a aliphatic alcohol content appropriate and beneficial to the next granulating step.

During the feed-mixing step, the reaction temperature is maintained preferably at a level at which at least the starting material comprising the non-reacted oxalic acid diester and the aliphatic alcohol in the reaction mixture can be maintained at a state of a melt and the content of the aliphatic alcohol in the reaction mixture can be maintained at 5 to 40% by weight.

Preferably, the reaction of the oxalic acid diester with ammonia is carried out at a temperature of from 30° C. above to 30° C. below, preferably 20° C. above to 20° C. below, the boiling point of the aliphatic alcohol to be evaporate-removed.

There is no limitation on the pressure under which the reaction is carried out.

In view of the ease of operation the reaction is preferably carried out under the ambient atmospheric pressure. The reaction may be carried out under a reduced pressure or an enhanced pressure, preferably under a pressure of from 10 Torr to 10 $kg/cm^2$ G.

The reaction rate can be enhanced by raising the, reaction pressure. However, an excessively high pressure is disadvantageous in terms of raised equipment cost.

In the process of the present invention, the granulating and drying steps may be carried out under a reduced pressure. When the drying step is carried out under a reduced pressure, a heat energy for drying can be reduced.

There is no limitation on the reaction time as far as the oxalic acid diester can be converted to oxamide with a high degree of purity under the above-mentioned reaction conditions. Preferably, the reaction time is 0.5 to 5 hours, more preferably 1 to 3 hours.

When the reaction is completed, the resultant reaction product in the state of a solid wetted by 5 to 40% by weight of the remaining aliphatic alcohol is directly subjected to a granulating step, without heat-drying the wetted reaction product.

Then, the resultant wetted reaction product granules are heated to evaporate away the aliphatic alcohol from the wetted granules and provide dry oxamide granules.

In the process of the present invention, if the reaction step, the granulating step and the drying steps can be carried out in one and the same apparatus, the oxamide granules can be produced by easy procedures. For this purpose, it is preferable that the reactor for the reaction step be provided with a stirring function and/or granulating function and further with an external cooling and heating jacket. Namely, this type of reactor can be utilized not only for the reaction step in which the reaction mixture is evenly stirred and maintained at a desired reaction temperature, but also for the granulating step in which the stirrer is used as a granulating device and the granulating system can be maintained at a desired temperature, and for the drying step in which the resultant granules are uniformly dried by using the stirrer and the external cooling and heating jacket. Accordingly, the process of the present invention is preferably carried out within an apparatus provided with a stirrer which can be utilized as a reaction-uniformalizing device in the reaction step and as a granulating device in the granulating step, and an external cooling and heating device which can be used as a temperature-control-device in the reaction step and the granulating and as a dryer in the drying step.

The use of the above-mentioned specific reaction-granulating-drying apparatus is advantageous in that in the reaction step, the gas-melt contact reaction of the starting material (comprising the oxalic acid diester and the aliphatic alcohol) with ammonia can be made uniform and accelerated, and in the granulating and drying steps, the reaction product in the state of a wetted solid can be easily and evenly granulated and dried in one and the same apparatus as that for the reaction step. Thus the resultant oxamide granules have an even quality. By using the above-mentioned apparatus, the process for producing the oxamide granules can be simplified and the expense of the oxamide granule-producing apparatus and the process cost can be reduced.

Of course, the reaction, granulating and drying steps can be carried out independently from each other in separate apparatuses in the case, for example, where the oxamide granules are produced in large amounts.

The process of the present invention can be, of course, carried out batchwise. Nevertheless, the process of the present invention can be conducted continuously by combining a continuous preparation of the oxalic acid diester-containing starting material melt with a continuous feed of the ammonia-containing gas, a continuous preparation of the reaction mixture and a continuous collection of the wetted solid oxamide with a high degree of purity.

In the process of the present invention, the concentration of the aliphatic alcohol in the reaction product fed to the granulating step is contributory to the final average size of the resultant oxamide granules. Therefore, the concentration of the aliphatic alcohol in the reaction product to be supplied to the granulating step is variable depending on the desired size of the final oxamide granules. In order to provide the oxamide granules having a desired size, the concentration of the aliphatic alcohol in the reaction mixture is controlled to a specific level in the range of from 5% to 40% by weight, depending on the desired size of the oxamide granules. Namely, the size of the oxamide granules can be controlled by controlling the concentration of the aliphatic alcohol in the reaction mixture. If the content of the aliphatic alcohol in the reaction product is less than 5% by weight, the resultant oxamide granules include an increased amount of small granules or particles having a size of 1.0 mm or less. Also, if the content of the aliphatic alcohol in the reaction product is more than 40% by weight, the resultant: reaction product exhibits an unsatisfactory granule-forming property. Generally, to provide oxamide granules having an average size of 2 to 4 mm, which is suitable for the use of the granules as granulated fertilizer, at a high yield, the content of the aliphatic alcohol in the reaction product to be fed to the granulating step is preferably controlled to a level of 10 to 30%, more preferably 15 to 25%, based on the total weight of the reaction product.

By controlling the content of the aliphatic alcohol in the reaction product during the reaction step to a level in the range of from 5% to 40% by weight, the resultant reaction product after the reaction step is completed, is in the state of wetted solid particles. The resultant wetted reaction product is successively fed into the granulating step. Before the granulating step, if necessary, the content of the aliphatic alcohol in the wetted reaction product is adjusted to a desired level in consideration of the desired size of the oxamide granules. This adjustment is carried out by controlling the temperature of the cooling and heating jacket equipped in the reaction apparatus. Also, the content of the aliphatic alcohol is controlled to a desired level within the range of from 5% to 40% by weight by evaporating away a portion of the aliphatic alcohol contained in the resultant reaction product or by adding a certain amount of the aliphatic alcohol to the resultant reaction product. Namely, in order to control the content of the aliphatic alcohol to a desired level, the real content of the aliphatic alcohol in the resultant reaction mixture is measured. If the real content is lower than the desired level, a portion of the aliphatic alcohol withdrawn from the reaction product is returned to the reaction mixture, to precisely adjust the content to the desired level. Also, if the real content is higher than the desired level, a portion of the aliphatic alcohol contained in the reaction product is evaporated away from the reaction product until the desired level is obtained.

The reaction product having a precisely adjusted content of the aliphatic alcohol is subjected to the granulating step.

After the content of the aliphatic alcohol is precisely adjusted, the temperature of the granulating system is preferably adjusted to a level right above or below the boiling point of the aliphatic alcohol, more preferably, 20° to 250° C. The granulating system may be under a reduced pressure or the same pressure as that in the reaction step. Preferably, the granulating step is carried out under a pressure of from 10 Torr to 10 $kg/cm^2$ G. The time for completing the granulation of the reaction product is preferably in a range of from 1 minute to 60 minutes. In the granulating step, the stirring rate for the granulation is variable depending on the type, form and capacity of the granulating vessel and the type and form of the stirring wings (blades). Preferably, the stirrer for the granulating step is selected from those by which the reaction product can be evenly granulated by revolving the stirring wings (blades) at a revolution rate of 10 to 500 rpm, into oxamide granules having an intended granule size.

In the process of the present invention, the feed-mixing step and the granulating steps or preferably successively carried out in one and the same vessel with mixing and/or granulating means.

After the granulating step is completed, the resultant wetted oxamide granules are subjected to a drying step to provide dry oxamide granules.

In the drying step, preferably, the revolution rate of the stirring wings (blades) is reduced to a low level of 1 to 200 rpm, and the oxamide granules are dried for a time of 0.5 to 2 hours under drying conditions under which the resultant oxamide granules are not crushed. The aliphatic alcohol remaining in the granules are substantially completely evaporated way and removed from the granules at a temperature equal to or above the boiling point of the aliphatic alcohol under the ambient pressure. The drying step can be carried out under an enhanced pressure, reduced pressure, or atmospheric pressure. Usually, the drying step is conducted under a pressure of from 10 Torr to 10 $kg/cm^2$ G, preferably a reduced pressure which effectively shortens the necessary drying time.

The resultant dry oxamide granules produced by the process of the present invention have a high degree of purity and a satisfactory resistance to crushing.

The drying procedure in the process of the present invention may be carried out in a drying apparatus separate from the reaction and granulating apparatus. In this case, the drying apparatus may be selected from conventional drying apparatuses, for example, conical dryers, rotary dryers, through-circulation conveyor dryers, through circulation rotation dryers, fluidizing bed dryers and vibration-fluidizing dryers. To condense and recover the aliphatic alcohol evaporated way from the oxamide granules, an indirect heating dryers are preferably employed rather than direct heating dryers in which hot air streams are used for drying.

In an embodiment of the process of the present invention, (D) the dry oxamide granules are re-wetted with water in an amount of 5 to 20% based on the weight of the dry oxamide granules; and then (E) re-drying the re-wetted oxamide granules by heating them to provide re-dried oxamide granules having an enhanced hardness and form-stability in water.

When the dry oxamide granules are subjected to the re-wetting step and the re-drying step, the content of the aliphatic alcohol in the dry oxamide granules is preferably controlled to a level of 0.1 to 5% based on the weight of the dry oxamide granules.

The above-mentioned small amount of the aliphatic alcohol remaining in the dry oxamide granules effectively accelerate the re-wetting rate of the dry oxamide granules with water, because the remaining aliphatic alcohol reduces the surface tension of water brought into contact with the dry oxamide granules in the re-wetting step, and thus water is introduced at an accelerated penetration rate into fine pores formed in the dry oxamide granules with a high efficiency. The content of the aliphatic alcohol remaining in the dry oxamide granules should be restrictively controlled to the above-mentioned level. If the dry oxamide granules contain the aliphatic alcohol at an excessively high content, the final re-drying step may require a complicated apparatus for recovering the aliphatic alcohol therefrom or a high cost for treating waste water discharged from the process of the present invention.

In the re-wetting step, water may be sprayed toward the dry oxamide granules or steam may be blown toward the dry oxamide granules. When the amount of water received by the oxamide granules is less than 5% by weight, the enhancing effect in hardness and form-stability in water, on the oxamide granules is unsatisfactory. Also, the amount of water is more than 20% by weight, the resultant oxamide granules exhibit a lowered rigidity and reduced mechanical properties. Accordingly, the amount of water to be applied to the dry oxamide granules must be within the above-mentioned specific range.

In the re-wetting step, the dry oxamide granules are preferably tumbled, stirred or fluidized while water or steam is applied to the granules through at least one spraying or blowing nozzle. The wetting procedure may be carried out in the drying apparatus in which the wetted reaction product granules are dried or by using a mixing apparatus separate from the drying apparatus. The mixing apparatus may be a tumbler type mixer or a stirrer type mixer. Otherwise, the re-we%ting step may be carried out while conveying the dry oxamide granules by using a feeder, for example, a conveyer belt or screw feeder.

In view of easy operation, the re-wetting step is preferably carried out under the ambient atmospheric pressure. However, the re-wetting pressure may be a reduced pressure or a raised pressure. Usually, the re-wetting step is carried out under a pressure of from 10 Torr to 10 kg/cm$^2$ G. To evenly introduce water or steam into the fine pores formed in the dry oxamide granules, it is preferable that the re-wetting step is carried out under a reduced pressure.

The application of the raised pressure does not provide any benefits and usually is disadvantageous in terms of increased cost of the re-wetting apparatus.

There is no limitation to the re-wetting temperature. Usually, the re-wetting step is carried out at a temperature of 5° to 180° C., preferably 20° to 90° C. When water is used, the re-wetting temperature is preferably 5° to 100° C., more preferably 10° to 90° C. When steam is utilized, the re-wetting step is carried out, preferably under a pressure of 0.5 to 20 kg/cm$^2$ G. Also, the steam is preferably a saturated steam.

After the re-wetting procedures are completed, the re-wetted oxamide granules may be immediately subjected to the re-drying step. However, the re-wetting oxamide granules are preferably aged for a time of 1 to 60 minutes, more preferably 2 to 30 minutes, to allow water or steam to sufficiently penetrate into the insides of the granules. This sufficient penetration of water or steam throughout the granules effectively enhances the hardness and mechanical strength of the resultant oxamide granules.

After the re-wetting procedures (optionally including an aging operation) are completed, the re-wetted oxamide granules are re-dried by heating the granules preferably at a temperature of 100° C. or more, more preferably 100° C. to 350° C., still more preferably 120° C. to 250° C., to evaporate away water from the granules preferably to an extent such that the content of water remaining in the granules reaches a level of about 2% by weight or less, more preferably 1.0% by weight or less, still more preferably 0.5% by weight or less.

The heat-drying procedure is continued preferably for a time of 3 minutes or more, more preferably 10 minutes or more, still more preferably 20 to 60 minutes, to reduce the water content of the granules to the intended level. When the drying step is completed in a short time less than 3 minutes, the hardness-enhancing effect for the oxamide granules sometimes becomes unsatisfactory.

During the heat-drying step, the re-wetted oxamide granules shrink and become dense with the reduction of the water content thereof, and as a result, the re-dried oxamide granules exhibit an enhanced hardness, mechanical strength (toughness) and water-resistance. Therefore, the re-drying step is very important to obtain toughened oxamide granules.

In view of the ease of the re-drying procedures, the re-drying step is preferably carried out under the ambient atmospheric pressure. If necessary, the re-drying step can be carried out under a pressurized condition. However, this is disadvantageous in that a pressure-resistant drying apparatus, which is expensive and causes an increased operation cost, must be employed.

In the re-drying step for the re-wetted oxamide granules, water is removed from the granules by evaporation preferably at a water-removing rate of 0.5 to 30 g/min, more preferably 1.0 to 15 g/min per kg of the granules. If the evaporation of water is carried out too fast, it sometimes becomes difficult to obtain oxamide granules having a satisfactory crushing strength.

The re-drying procedures for the re-wetted oxamide granules may be carried out batchwise by using the same heat-drying apparatus as that used for drying the reaction product granules wetted by the aliphatic alcohol.

When the oxamide granules are produced in a large amount, the re-drying step is preferably carried out continuously by using another heat-drying apparatus.

The heat-drying apparatus for the re-drying step may be selected from direct heat-drying apparatuses in which hot air or overheated steam is used as a heating medium, for example, rotary dryers, through-circulation type rotation dryers, fluidized bed dryers, vibration-fluidized bed dryers, and through-circulating type band dryers; indirect heat-drying apparatuses in which steam or another heating medium is used, for example, conical dryers, rotary dryers, agitation type dryers and vibration dryers.

The process of the present invention enables the dry oxamide granules having a high degree of purity and a satisfactory toughness, crushing strength and water-resistance to be produced at a high efficiency without employing a binder.

EXAMPLES

The present invention will be further explained by the following specific examples.

Example 1

A mixer equipped with a cooling and heating jacket and stirring wings and having an effective capacity of 10 liters was used as an apparatus for producing oxamide granules.

The inside space of the apparatus was filled by a nitrogen gas, and charged with a mixture of 6 kg of dimethyl oxalate and 2.91 kg of methyl alcohol while flowing a heating medium consisting of a silicone oil at a temperature of 64° C. through the jacket, to provide a melt of a starting material. An ammonia gas was fed-mixed to the starting material melt in the apparatus at a feed rate of 5.39 Nm$^3$/hr, while stirring the resultant reaction mixture at a revolution rate of the stirring wings of 200 rpm. The reaction of dimethyl oxalate with ammonia was started.

With the progress of the reaction, reaction heat was generated, and the methyl alcohol in the reaction mixture was evaporated in an amount corresponding to the amount of the generated reaction heat. The evaporated fraction of the methyl alcohol was discharged together with a non-reacted ammonia gas fraction to the outside of the apparatus through a discharge conduit. The discharged mixture gas of methyl alcohol with the non-reacted ammonia was introduced into a condenser and cool-condensed in the condenser to separate the condensed methyl alcohol from the mixture gas.

During the reaction, the pressure in the apparatus was maintained equal to the ambient atmospheric pressure, and the temperature of the heating medium in the jacket was maintained at 64° C. Under these conditions, the amount of the generated reaction heat was balanced with the amount of the evaporation heat of methyl alcohol, and thus the temperature of the reaction mixture was maintained within the range of from 64° C. to 70° C.

The introduction of the ammonia gas was continuously carried out at the above-mentioned feed rate for 77 minutes to complete the reaction, and thereafter stopped.

In the feed mixing step, the content of methyl alcohol in the reaction mixture was controlled from 32.7% (at the start) to 22.6% (at the end) based on the total weight of the reaction mixture.

At the stage of 72 minutes after the start of the introduction of the ammonia gas, the granulation of the resultant reaction product was startled and completed 5 minutes after the start of the granulation.

As mentioned above, the oxamide-producing reaction was substantially completed by the reaction procedures for 72 minutes. However, to ensure the completion of the reaction, the introduction of the ammonia gas was continued for 77 minutes.

The resultant reaction product granules contained 18.3% by weight of methyl alcohol and thus was in the state of wetted solid granules.

The reaction product granules was subjected to a drying step to substantially completely remove methyl alcohol therefrom.

In the drying step, the revolution rate of the stirring wings was reduced to 15 rpm, and the temperature of the heating medium in the jacket was raised to 150° C. The drying procedures were carried out at a temperature of 150° C. for 60 minutes while revolving the stirring wings, to remove methyl alcohol. The dried oxamide granules were obtained in an amount of 4.43 kg and contained substantially no methyl alcohol.

The oxamide granules were classified by using JIS standard selves having a hole size of 2 mm, 2.8 mm, 3.35 mm, 4 mm, 4.75 mm and 5.6 mm, and the amounts of the classified fractions were measured. The weight average size of the granules was calculated in accordance with the equation (I):

$$d = \left(1 \times W_1 + \frac{1+2}{2} \times W_2 + \frac{2+2.8}{2} \times W_3 + \frac{2.8+3.35}{2} \times W_4 + \frac{3.35+4}{2} \times W_5 + \frac{4+4.75}{2} \times W_6 + \frac{4.75+5.6}{2} \times W_7 + 5.6 \times W_8\right) / (W_1 + W_2 + W_3 + W_4 + W_5 + W_6 + W_7 + W_8) \quad (I)$$

wherein d represents a weight average size of the granules, and $W_1$, $W_2$, $W_3$, $W_4$, $W_5$, $W_6$, $W_7$ and $W_8$ respectively represent an amount of a fraction of the granules having a size S of less than 1 mm, 1 mm or more but less than 2 mm, 2 mm or more but less than 2.8 mm, 2.8 mm or more but less than 3.35 mm, 3.35 mm or more but less than 4.0 mm, 4.0 mm or more but less than 4.75 mm, 4.75 mm or more but less than 5.6 mm and 5.6 mm or more, as shown below.

| Size S of granule (mm) | Weight |
|---|---|
| $S < 1$ | $W_1$ |
| $1 \leqq S < 2$ | $W_2$ |
| $2 \leqq S < 2.8$ | $W_3$ |
| $2.8 \leqq S < 3.35$ | $W_4$ |
| $3.35 \leqq S < 4.0$ | $W_5$ |
| $4.0 \leqq S < 4.75$ | $W_6$ |
| $4.75 \leqq S < 5.6$ | $W_7$ |
| $5.6 \leqq S$ | $W_8$ |

As a result, the weight average size of the oxamide granules was 2.69 mm, and the content of a fraction of the granules having a size of from 2.0 to 4.0 mm was 71.9% based on the total weight of the granules.

Examples 2 to 4

In each of Examples 2 to 4, the same procedures as in Example 1 were carried out except that dimethyl oxalate, and methyl alcohol were used in the amounts as shown in Table 1 to provide the starting material and the ammonia gas was introduced into the apparatus at the feed rate as shown in Table 1.

In each of Examples 2 and 4, the drying procedures were carried out by using a rotary evaporator having a capacity of 20 liters. Namely in Examples 2 and 4, the reaction and granulating procedures were carried out in the same agitation type granulating apparatus equipped with the heating and cooling jacket as in Example 1, and the resultant wetted reaction product granules were transferred into the evaporator. In Example 2, the granules were dried at a heating bath temperature of 120° C. under the ambient atmospheric pressure for 60 minutes. Also, in Example 4, the granules were dried at a heating bath temperature of 95° C. under a reduced pressure of 350 Torr for 60 minutes. The reaction conditions, the content of methyl alcohol in the reaction product, the contents of fractions of the resultant granules having a size of 2 mm or less, 2 mm or more but less than 4 mm and 4 mm or more, and the average size of the resultant granules are shown in Table 1.

Examples 5 to 10

In each of Examples 5 to 10, the same procedures as in Example 1 were carried out with the following exceptions.

The oxamide granule-producing process was carried out by using an agitation type mixer equipped with a heating and cooling jacket and having an effective capacity of 50 liters.

The amounts of dimethyl oxalate and methyl alcohol, the feed rate of the ammonia gas, the reaction pressure and the revolution rate of the stirring wings in the reaction step were changed to those as shown in Table 1.

In Example 8, the drying step was carried out at a heating medium temperature of 95° C. under a reduced pressure of 350 Torr.

In each of Examples 6 and 7, only the drying step was carried out by using the same 20 liter rotary evaporator as in Example 2.

In each of Examples 9 and 10, only the drying step was carried out by using the same rotary evaporator as in Example 4.

The operational conditions and the results of each of Examples 5 to 10 are shown in Table 1.

From the results of Examples 1 to 10, a relationship between the content of methyl alcohol in the reaction product fed to the granulating step and the average size of the resultant dry oxamide granules was as shown in FIG. 1.

Figure 2:
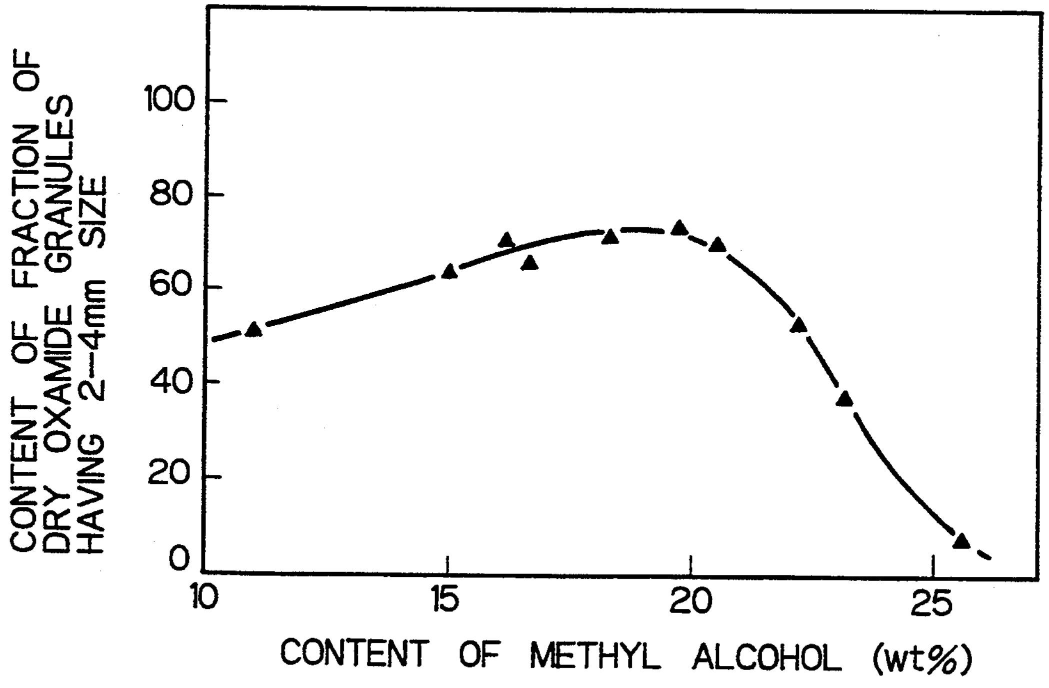
FIG. 2 is a graph showing a relationship between the content of methyl alcohol in the reaction product and the content of a fraction of the granules having a size of from 2 to 4 mm based on the total weight of the resultant dry oxamide granules in Examples 1 to 10.

Also, FIG. 2 shows a relationship between the content of methyl alcohol in the reaction product fed to the granulating step and the content (%) of a fraction of the granules having a size of from 2.0 mm to 4.0 mm in the resultant dry oxamide granules, obtained in Examples 1 to 10.

Comparative Example 1

The same procedures as in Example 1 were carried out with the following exceptions.

In the reaction step, the pressure in the apparatus was maintained at a level of 0.5 kg/cm$^2$ G, while 10 maintaining the heating medium temperature at a level of 64°

C. Therefore, the content of methyl alcohol in the reaction mixture increased with the progress of the reaction. The ammonia gas was continuously fed into the apparatus for 90 minutes and then the feeding of the ammonia gas was stopped. When stopped, the reaction had been completed, and the resultant reaction product contained methyl alcohol in an excessive amount of 40.1% by weight. The reaction product was in the form of a lump.

A granulating procedure was applied to the reaction product at a revolution rate of the stirring wings of 200 rpm for 30 minutes. The reaction product could not be satisfactorily granulated.

The results are shown in Table 1.

Comparative Example 2

The same procedures as in Comparative Example 1 were carried out with the following exceptions.

In the preparation of the starting material, methyl alcohol was employed in an amount of 1.5 kg. In the reaction step, the heat medium temperature in the jacket was controlled to 75° C. The reaction was completed by feeding the ammonia gas for 82 minutes. The resultant reaction product contained methyl alcohol in an content of 2.3% by weight. After the granulating and drying steps were completed, it was found that the resultant dry oxamide was in the form of a mixture of small granules and fine particles having a size of 0.5 mm or less.

Example 11

An agitation type granulating apparatus equipped with a heating and cooling jacket and having an effective capacity of 50 liters was used as an apparatus for producing dry oxamide granules.

The inside space of the apparatus was filled by a nitrogen gas, while flowing a heating medium at a temperature of 64° C. through the jacket, then 30 kg of dimethyl oxalate and 18 kg of methyl alcohol were charged into the apparatus. The resultant mixture was heat-melted at a temperature of 64° C., to provide a starting material melt. To the starting material melt was feed-mixed an ammonia gas at a feed rate of 20.5 $Nm^3/hr$, while stirring the reaction mixture by revolving stirring wings at a revolution rate of 160 rpm, to start an ammonia-addition, decomposing reaction.

The pressure in the inside of the apparatus was maintained at a level of 0.3 $kg/cm^2$ G, and the temperature of the heating medium flowing through the jacket was maintained at 70° C., during the reaction step. With the progress of the reaction, a reaction heat was generated to cause methyl alcohol contained in the reaction mixture to be evaporated in an amount corresponding to the amount of the generated heat and discharged together with non-reacted ammonia gas fraction through a discharge conduit to the outside of the apparatus. The

TABLE 1

| Item | Composition of starting material (kg) | | | Process conditions | | | | | Content of methyl alcohol in | Product: Granule size distribution (wt %) | | | |
|---|---|---|---|---|---|---|---|---|---|---|---|---|---|
| Example No. | Dimethyl oxalate | Methyl alcohol | Feed rate of ammonia gas ($Nm^3/hr$) | Heating medium temperature (°C.) | Pressure in apparatus ($kg/cm^2G$) | Revolution rate of stirring wings (rpm) | Time (min) Reaction | Time (min) Granulating | reaction product (wt %) | 2 mm or less | 4 mm or less but more than 2 mm | More than 4 mm | Average size of granules (mm) |
| Example | | | | | | | | | | | | | |
| 1 | 6.0 | 2.91 | 5.39 | 64 | 0 | 200 | 72 | 5 | 18.3 | 18.1 | 71.9 | 10.0 | 2.69 |
| 2 | 6.0 | 2.91 | 3.85 | 64 | 0 | 200 | 110 | 9 | 19.7 | 14.2 | 73.5 | 12.3 | 2.84 |
| 3 | 6.0 | 4.00 | 4.20 | 64 | 0 | 200 | 81 | 8 | 23.1 | 2.0 | 37.3 | 60.7 | 4.22 |
| 4 | 6.0 | 4.00 | 4.00 | 64 | 0 | 200 | 85 | 9 | 25.6 | 2.6 | 7.6 | 89.8 | 5.03 |
| 5 | 30.0 | 16.0 | 20.5 | 72 | 0.3 | 200 | 48 | 5 | 11.0 | 49.4 | 50.6 | 0 | 1.92 |
| 6 | 24.0 | 12.0 | 20.5 | 73 | 0.3 | 120 | 43 | 5 | 15.0 | 33.0 | 63.4 | 3.6 | 2.36 |
| 7 | 24.0 | 13.0 | 20.5 | 70 | 0.3 | 120 | 48 | 5 | 16.6 | 32.0 | 65.3 | 2.7 | 2.35 |
| 8 | 30.0 | 14.7 | 25.7 | 70 | 0.4 | 120 | 48 | 5 | 16.1 | 27.4 | 71.0 | 1.6 | 2.38 |
| 9 | 30.0 | 16.0 | 20.5 | 71 | 0.4 | 120 | 65 | 5 | 20.5 | 12.5 | 70.1 | 17.4 | 3.08 |
| 10 | 30.0 | 17.1 | 20.5 | 71 | 0.4 | 120 | 61 | 5 | 22.2 | 12.2 | 52.9 | 34.9 | 3.40 |
| Comparative Example | | | | | | | | | | | | | |
| 1 | 6.0 | 2.91 | 5.39 | 64 | 0.5 | 200 | 90 | 30 | 40.1 | The granulation was unsuccessful and the product was in the form of a lump | | | |
| 2 | 6.0 | 1.5 | 5.39 | 75 | 0.5 | 200 | 70 | 12 | 2.3 | The granulation was unsuccessful and the product was in the form of small granules or a fine powder | | | |

As clearly shown in Table 1, by the process of the present invention, the oxamide granules having a high degree of purity and a desired average size can be produced by simple procedures without employing a binder.

The resultant oxamide granules are useful as a slow release fertilizer.

discharged mixture of the methyl alcohol with ammonia was cooled in a condenser, and the condensed methyl alcohol was removed from the discharged mixture. To complete the reaction, the ammonia gas was continuously introduced into the apparatus at the above-mentioned feed rate for 66 minutes, and then the introduction of the ammonia gas was stopped. During the reaction, the content of methyl alcohol in the reaction mixture was controlled from 37.5% by weight to 21.3% by weight.

After the completion of the reaction step, the revolution rate of the stirring wings was changed to 120 rpm, and the resultant reaction product in the state of a solid powder wetted by 21.3% by weight of methyl alcohol was granulated by revolving the stirring wings. The granulation was completed 5 minutes after the start of the revolving operation of the stirring wings.

The resultant wetted reaction product granules contained 21.3% by weight of methyl alcohol.

Then, the wetted reaction product granules were subjected to a drying step in the apparatus to substantially completely remove methyl alcohol from the granules.

In the drying step, the revolution rate of the stirring wings was lowered to 10 rpm and the heating medium temperature of the jacket was raised to 120° C. The drying step was carried out under a pressure of 550 Torr for 40 minutes.

The resultant dried oxamide granules with a high degree of purity were obtained in an amount of 22 kg. In the dry granules, methyl alcohol was not substantially detected. The dry oxamide granules were subjected to a measurement of crushing strength. As the result of a test in which 30 granules having a size of 3.35 to 4.0 mm were crushed, the average crushing strength of the granules was 1.1 kg per granule.

In the next step, the pressure in the inside of the apparatus was made equal to the ambient atmospheric pressure, and the temperature of the heating medium in the jacket was adjusted to 80° C. The dry oxamide granules in the apparatus were evenly wetted with 2.2 kg (corresponding to 10% of the total weight of the granules) of water at a temperature of 15° C. by spraying water toward the granules.

Then, the temperature of the heating medium in the jacket was raised to 150° C. The wetted granules in the apparatus were heat-dried while revolving the stirring wings at the above-mentioned revolution rate of 10 rpm for 40 minutes.

The resultant re-dried oxamide granules had a water content of 0.1% by weight or less and an average size of 3.4mm.

In the result of the crushing strength test for 30 granules having a size of 3.55 to 4.0 mm, it was confirmed that the average crushing strength was enhanced from 1.1 kg to 2.7 kg per granule.

Example 12

The same procedures as in Example 11 were carried out with the following exceptions.

The revolution rate of the stirring wings in the reaction and granulating steps were changed to 120 rpm. The resultant reaction product had a content of methyl alcohol of 23.1% by weight. The drying step was carried out by using a 20 liter rotary evaporator. Namely, the reaction and granulating steps were carried out by using the same agitation type granulation apparatus with a heating and cooling jacket as that in Example 11, and then the drying step was carried out batchwise by charging 8 kg of the resultant reaction product per batch into the rotary evaporator and rotating the evaporator at a rotation rate of 10 rpm at a heating bath temperature of 120° C. under the ambient atmospheric pressure for 60 minutes. Dried oxamide granules having a high degree of purity were obtained in an amount of 22 kg. In the resultant dry granules, no methyl alcohol was detected. These dry granules had a crushing strength of 1.3 kg per granule.

The dry oxamide granules in an amount of 150 g were placed in a 500 ml rotary evaporator equipped with two lifting flights attached to the inside face of the evaporator, and the evaporator was rotated at a rotation rate of 10 rpm, while spraying water in an amount of 7.5g corresponding to 5% of the weight of the granules toward the granules. The water to be sprayed had a temperature of 15° C.

This re-wetting step was carried out at room temperature under the ambient atmospheric pressure. Immediately after the re-wetting step was completed, the evaporator was placed in a heating oil bath at a temperature of 150° C., and rotated at a rotation rate of 30 rpm under the ambient atmospheric pressure for 30 minutes to re-dry the re-wetted oxamide granules while tumbling the granules.

The resultant re-dried axamide granules had a similar average size to that in Example 11 and a content of water of 0.1% by weight or less.

Also, the resultant oxamide granules had a crushing strength of 1.9 kg per granule.

Example 13

The same procedures as in Example 12 were carried out with the following exceptions. In the re-wetting step for the dry oxamide granules, the amount of water applied to the granules was 15 g corresponding to 10% of the total weight of the dry granules, the re-drying step was carried out for 60 minutes.

The resultant re-dried oxamide granules had a similar average size to that in Example 11 and the content of water in the re-dried granules was 0.1% by weight or less.

The re-dried oxamide granules had a crushing strength of 2.2 kg per granule.

Example 14

The same procedures as in Example 12 were carried out with the following exceptions.

In the re-wetting step, the amount of the sprayed water was 22.5 g corresponding to 15% of the total weight of the dry oxamide granules, and the re-drying time was 70 minutes.

The resultant re-dried oxamide granules had a similar average size to that in Example 11 and contained water in an amount of 0.1% by weight or less.

The re-dried oxamide granules had a crushing strength of 2.3 kg per granule.

Example 15

The same procedures as in Example 12 were carried out with the following exceptions.

In the re-wetting step, the amount of the sprayed water was 30 g corresponding to 20% of the total weight of the dry oxamide granules, and the re-drying time was 70 minutes.

The resultant re-dried oxamide granules had a similar average size to that in Example 11 and contained water in an amount of 0.1% by weight or less.

The re-dried oxamide granules had a crushing strength of 1.7 kg per granule.

Example 16

The same procedures as in Example 13 were carried out with the following exceptions.

In the re-drying step, the heating bath temperature was 120° C., and the re-drying time was 75 minutes.

The resultant re-dried oxamide granules had a similar average size to that in Example 11 and contained water in an amount of 0.1% by weight or less.

The re-dried oxamide granules had a crushing strength of 1.8 kg per granule.

Example 17

The same procedures as in Example 13 were carried out with the following exceptions.

In the re-wetting step, the re-wetted granules were aged at a temperature of 80° C. for 30 minutes in a closed container.

The resultant re-dried oxamide granules had a similar average size to that in Example 11 and contained water in an amount of 0.1% by weight or less.

The re-dried oxamide granules had a crushing strength of 2.9 kg per granule.

Example 18

The same reaction, granulating and drying procedures as in Example 12 were carried out with the following exceptions.

In the drying step for the granulation product, the drying time was changed to 13 minutes, and the dry oxamide granules had a methyl alcohol content of 1.53% by weight and a crushing strength of 0.5 kg per granule. The dry oxamide granules were subjected to the same rewetting and re-drying steps in Example 13.

The resultant re-dried oxamide granules had a similar average size to that in Example 11 and contained water in an amount of 0.1% by weight or less.

The re-dried oxamide granules had a crushing strength of 3.0 kg per granule.

Example 19

The same reaction, granulating and drying procedures as in Example 12 were carried out with the following exceptions.

In the drying step for the granulation product, the drying time was changed to 23 minutes. The resultant dry oxamide granules had a methyl alcohol content of 0.78% by weight and a crushing strength of 0.9 kg per granule.

The resultant dry oxamide granules was subjected to the same re-wetting and re-drying steps as in Example 13. The resultant re-dried oxamide granules had a similar average size to that in Example 11 and contained water in an amount of 0.1% by weight or less.

The re-dried oxamide granules had a crushing strength of 2.8 kg per granule.

Example 20

The same reaction, granulating and drying procedures as in Example 12 were carried out with the following exceptions.

In the drying step for the granulation product, the pressure in the apparatus was changed to 200 Torr. In the resultant dry oxamide granules, no methyl alcohol was detected. The dry oxamide granules had a crushing strength of 1.0 kg per granule.

The same re-wetting and re-drying procedures as in Example 13 were applied to the dry oxamide granules.

The resultant re-dried oxamide granules had a similar average size to that in Example 11 and contained water in an amount of 0.1% by weight or less.

The re-dried oxamide granules had a crushing strength of 2.3 kg per granule.

Example 21

The same procedures as in Example 20 were carried out with the following exceptions.

In the re-wetting step, water was applied to the dry oxamide granules under a pressure of 20 Torr.

The resultant re-dried oxamide granules had a similar average size to that in Example 11 and contained water in an amount of 0.1% by weight or less.

The re-dried oxamide granules had a crushing strength of 2.6 kg per granule.

Example 22

The same reaction, granulating and drying procedures as in Example 11 were carried out with the following exceptions.

In the preparation of the starting material, dimethyl oxalate and methyl alcohol were employed in amounts of 30 kg and 17.1 kg, respectively.

In the reaction step, the reaction pressure in the apparatus was adjusted to 0.4 kg/cm$^2$ G, the revolution rate of the stirring wings was 120 rpm and the reaction time was 61 minutes.

The resultant reaction product granules from the granulating step had a methyl alcohol content of 22.2% by weight. The reaction product granules were dried in the same manner as in Example 12. In the resultant dry oxamide granules, no methyl alcohol was detected. Also, the dry oxamide granules had a crushing strength of 1.1 kg per granule.

The above-mentioned dry oxamide granules were placed in a container made from a metallic net, and a saturated steam having a pressure of 4 kg/cm$^2$ G was blown toward the granules for 20 minutes to re-wet the granules. The re-wetted granules had a water content of 7.6% by weight based on the total weight of the re-wetted granules.

After the re-wetting procedures were completed, the re-wetted granules were transferred from the metal net container to a 500 ml rotary evaporator, and re-dried at a heating bath temperature of 150° C. under the ambient atmospheric pressure for 60 minutes while rotating the evaporator at a rotation rate of 30 rpm.

The resultant re-dried oxamide granules had a similar average size to that in Example 11, a water content of 0.1% by weight or less, and an enhanced crushing strength of 2.8 kg per granule.

Example 23

The same reaction, granulating and drying procedures as in Example 11 were carried out with the following exceptions.

In the preparation of the starting material, dimethyl oxalate and methyl alcohol were employed in amounts of 24 kg and 14 kg, respectively.

In the reaction step, the heating medium temperature in the jacket was adjusted to 73° C., the revolution rate of the stirring wings was 120 rpm and the reaction time was 43 minutes.

The resultant reaction product granules from the granulating step had a methyl alcohol content of 20.5% by weight. The reaction product granules were dried by using an indirectly heating, groove type agitation-dryer (effective capacity: 50 liters, heating area: 1.9m$^2$). This dryer was equipped with a heating jacket and heated by steam. Also, in this dryer, a horizontal rotable stirring shaft and 10 disks attached to the shaft were hollow and heated by steam.

The reaction product granules having a methyl alcohol content of 20.5% by weight were placed in an amount of 22.2 kg in the above-mentioned indirectly heating type, groove type agitation dryer, the jacket and the rotable disks were heated at a temperature of 120° C. by flowing steam therethrough under a pressure of 1.9 kg/cm$^2$ G. The disks were revolved at a revolution rate of 20 rpm. The granules were dried in the dryer 10 under the ambient atmospheric pressure for 60 minutes.

The resultant dry oxamide granules had a methyl alcohol content of 1.1% by weight and a crushing strength of 1.3 kg per granule.

The above-mentioned dry oxamide granules were re-wetted with 1.8 kg (corresponding to 10% of the total weight of the granules) of water at a temperature of 20° C. by spraying water thereto while stirring the granules in the dryer.

After the re-wetting procedures were completed, the re-wetted granules were re-dried in the dryer in which the temperature of the jacket and rotable disks was maintained at 150° C. by flowing steam under a pressure of 5 kg/cm$^2$ G, and the rotable disks were revolved at a revolution rate of 20 rpm, under the ambient atmospheric pressure for 45 minutes.

The resultant re-dried oxamide granules had the similar average size to that in Example 11, a water content of 0.7% by weight, and an enhanced crushing strength of 3.2 kg per granule.

Example 24

The same reaction, granulating and drying procedures as in Example 11 were carried out with the following exceptions.

In the preparation of the starting material, dimethyl oxalate and methyl alcohol were employed in amounts of 30 kg and 13.5 kg, respectively.

In the reaction step and the granulating step, the pressure in the apparatus was adjusted to 0.5 kg/cm$^2$ G, the revolution rate of the stirring wings was 120 rpm and the reaction time was 53 minutes.

The resultant reaction product granules from the granulating step had a methyl alcohol content of 18.7% by weight. The reaction product granules were dried in the same manner as in Example 12, except that the heating bath temperature was 90° C., the pressure in the dryer was 350 Torr and the drying time was 90 minutes. In the resultant dry oxamide granules, no methyl alcohol was detected and the crushing strength of the granules was 1.2 kg per granule.

The dry oxamide granules were re-wetted with water while feeding the granules at a feed rate of 130 kg/hr into a rotary dryer through a screw feeder. Water was splayed at a temperature of 20° C. toward the granules through a spraying nozzle attached to a middle portion of the screw feeder.

The re-wetted oxamide granules had a water content of 9 to 11% based on the weight of the re-wetted granules.

The re-wetted granules were continuously fed into the rotary dryer through the screw feeder and heat-dried in the dryer. This rotary dryer was a hot air-heating type rotary dryer having a diameter of 0.5 mm and a length of 2.8 m and equipped with a plurality of lifting flights attached to the inside wall surface of the drum. The drum was rotated at a rotation rate of 8 rpm and hot air of a temperature 630° C. was blown cocurrently with the path of the granules. The residing time of the granules in the dryer was 11 minutes.

The resultant re-dried oxamide granules had the similar average size to that in Example 11, a water content of 0.2% by weight, and an enhanced crushing strength of 2.8 kg per granule.

Example 25

The same procedures as those in Example 13 were carried out except that the re-wetting step was omitted. The resultant oxamide granules exhibited a crushing strength of 1.4 kg per granule.

Process conditions of Examples 11 to 25

The conditions and results in the steps of the processes of Examples 11 to 25, are shown in Table 2.

The crushing strength (toughness) of the oxamide granules was indicated by an average of measured values of 30 granules having a size of 3.35 to 4.0 mm. The measurement of the crushing strength was carried out by using a Kiya type crushing strength tester.

Evaluating of the oxamide granules as a slow release fertilizer

The re-dried oxamide granules obtained in each of Examples 11 to 25 were subjected to a test for powdering property of the granule surfaces and a test for form-stability in water.

The powdering property of the granule surfaces was evaluated by hand-touching the granules and observing whether or not powder adhered to the hand.

The form-stability of the granules in water was evaluated by immersing 100 granules in 500 ml of water at room temperature, leaving them in water for 2 weeks and observing whether or not the granules were collapsed.

The test results are shown in Table 3.

TABLE 2

| Example No. | Reaction, granulating & drying steps: $CH_3OH$ content in reaction product (wt %) | $CH_3OH$ drying conditions: Temperature (°C.) | Pressure (Torr) | Time (Min) | $CH_3OH$-dried granules: $CH_3OH$ content (wt %) | Crushing strength (Kg/granule) | Re-wetting & re-drying steps: Water content added to dried granules (wt %) | Re-drying conditions: Temperature (°C.) | Pressure | Time (Min) | Re-dried granules: Water content (wt %) | Crushing strength (Kg/granule) |
|---|---|---|---|---|---|---|---|---|---|---|---|---|
| Example | | | | | | | | | | | | |
| 11 | 21.3 | 120 | 550 | 40 | 0 | 1.1 | 10 | 150 | (*)1 | 40 | <0.1 | 2.7 |
| 12 | 23.1 | 120 | (*)1 | 60 | 0 | 1.3 | 5 | 150 | (*)1 | 30 | <0.1 | 1.9 |
| 13 | 23.1 | 120 | (*)1 | 60 | 0 | 1.3 | 10 | 150 | (*)1 | 60 | <0.1 | 2.2 |
| 14 | 23.1 | 120 | (*)1 | 60 | 0 | 1.3 | 15 | 150 | (*)1 | 70 | <0.1 | 2.3 |

TABLE 2-continued

| | Reaction, granulating & drying steps | | | | | | Re-wetting & re-drying steps | | | | Re-dried granules | |
|---|---|---|---|---|---|---|---|---|---|---|---|---|
| | $CH_3OH$ content in reaction product | $CH_3OH$ drying conditions | | | $CH_3OH$-dried granules | | Water content added to dried granules | Re-drying conditions | | | | |
| Example No. | (wt %) | Temperature (°C.) | Pressure (Torr) | Time (Min) | $CH_3OH$ content (wt %) | Crushing strength (Kg/granule) | (wt %) | Temperature (°C.) | Pressure | Time (Min) | Water content (wt %) | Crushing strength (Kg/granule) |
| 15 | 23.1 | 120 | $(*)_1$ | 60 | 0 | 1.3 | 20 | 150 | $(*)_1$ | 70 | <0.1 | 1.7 |
| 16 | 23.1 | 120 | $(*)_1$ | 60 | 0 | 1.3 | 10 | 120 | $(*)_1$ | 75 | <0.1 | 1.8 |
| 17 | 23.1 | 120 | $(*)_1$ | 60 | 0 | 1.3 | 10 | 150 | $(*)_1$ | 60 | <0.1 | 2.9 |
| 18 | 23.1 | 120 | $(*)_1$ | 13 | 1.53 | 0.5 | $(*)_2$ 10 | 150 | $(*)_1$ | 60 | <0.1 | 3.0 |
| 19 | 23.1 | 120 | $(*)_1$ | 23 | 0.78 | 0.9 | 10 | 150 | $(*)_1$ | 60 | <0.1 | 2.8 |
| 20 | 23.1 | 120 | 200 | 60 | 0 | 1.0 | 10 | 150 | $(*)_1$ | 60 | <0.1 | 2.3 |
| 21 | 23.1 | 120 | 200 | 60 | 0 | 1.0 | 10 | 150 | $(*)_1$ | 60 | <0.1 | 2.6 |
| 22 | 22.2 | 120 | $(*)_1$ | 60 | 0 | 1.1 | $(3)_2$ 8.2 | 150 | $(*)_1$ | 60 | <0.1 | 2.8 |
| 23 | 20.5 | 120 | $(*)_1$ | 60 | 1.1 | 1.3 | $(*)_4$ 10 | 150 | $(*)_1$ | 45 | 0.7 | 3.2 |
| 24 | 18.7 | 90 | 350 | 90 | 0 | 1.2 | 9.9 ~ 12.4 | 630 | $(*)_1$ | 11 | 0.2 | 2.8 |
| 25 | 23.1 | 120 | $(*)_1$ | 60 | 0 | 1.3 | 0 | 150 | $(*)_1$ | 60 | — | 1.4 |

Note:
$(*)_1$The ambient atmospheric pressure.
$(*)_2$The re-wetted granules were aged at 80° C. for 30 minutes.
$(*)_3$The re-wetting procedure with water was carried out under a pressure of 20 Torr.
$(*)_4$The re-wetting precedure was carried out by applying steam.

TABLE 3

| Item Example No. | Powdering phenomenon of granule surface | Form-stability in water |
|---|---|---|
| Example | None | No collapse |
| 11 | None | No collapse |
| 12 | None | No collapse |
| 13 | None | No collapse |
| 14 | None | No collapse |
| 15 | None | No collapse |
| 16 | None | No collapse |
| 17 | None | No collapse |
| 18 | None | No collapse |
| 19 | None | No collapse |
| 20 | None | No collapse |
| 21 | None | No collapse |
| 22 | None | No collapse |
| 23 | None | No collapse |
| 24 | None | No collapse |
| 25 | None | Collapsed in about 5% |

As clearly shown in Tables 2 and 3, the process of the present invention, in which the reaction, granulating and drying steps are followed by a water-rewetting step and a re-drying step, effectively produce oxamide granules with a high degree of purity, a high crushing strength and a high form-stability in water, with a high yield. The resultant oxamide granules are useful as a slow release fertilizer.

We claim:

1. A process for producing oxamide granules comprising the step of:

(A) feed-mixing an ammonia-containing gas to a melt of a starting material comprising 60 to 100% by weight of an oxalic acid diester of the formula (I):

COOR
|
COOR (I)

wherein R represents a lower alkyl group having 1 to 6 carbon atoms, and about 2 to 40% by weight of an aliphatic alcohol having 1 to 6 carbon atoms, to cause the oxalic acid diester to react with ammonia and produce oxamide and a by-product consisting of an aliphatic alcohol having the same alkyl group as that represented by R in the formula (I), while controlling the content of the aliphatic alcohol in the reaction mixture to a level of 5 to 40% based on the weight of the reaction mixture to provide a reaction product in the state of a wetted solid and comprising the resultant oxamide and the aliphatic alcohol;

(B) granulating the wetted reaction product into a plurality of granules, while maintaining the content of the aliphatic alcohol at a level of 5 to 40% based on the weight of the wetted reaction product; and (C) drying the resultant wetted oxamide granules by heat-evaporating away the aliphatic alcohol therefrom, to provide dry oxamide granules.

2. The process as claimed in claim 1, wherein the starting material is melted at a temperature of from 40° C. to 160° C.

3. The process as claimed in claim 1, wherein the ammonia-containing gas contains ammonia in a content of 50% by volume or more.

4. The process as claimed in claim 1, wherein the reaction of the oxalic acid diester with ammonia is carried out at a temperature of from 30° C. above to 30° C. below the boiling point of the aliphatic alcohol.

5. The process as claimed in claim 1, wherein the control of the content of the aliphatic alcohol in the feed-mixing step (A) is carried out by evaporate-removing the aliphatic alcohol from the reaction mixture.

6. The process as claimed in claim 1, wherein the feed-mixing step (A) is carried out while stirring the reaction mixture.

7. The process as claimed in claim 1, wherein the granulating step (B) is carried out by stirring the resultant wetted reaction product at a temperature of 20° C. to 250° C.

8. The process as claimed in claim 1, wherein in the granulating step (B), the wetted reaction product contains the aliphatic alcohol in an amount of 10 to 30% by weight.

9. The process as claimed in claim 1, wherein the feed-mixing step (A) and the granulating step (B) are successively carried out in one and the same vessel with mixing and/or granulating means.

10. The process as claimed in claim 1, further comprising the steps of:

(D) re-wetting the dry oxamide granules with water in an amount of 5 to 20% based on the weight of the dry oxamide granules; and (E) re-drying the re-wetted oxamide granules by heating to provide oxamide granules having an enhanced hardness and form-stability in water.

11. The process as claimed in claim 10, wherein the rewetting step is carried out at a temperature of 5° to 180° C.

12. The process as claimed in claim 10, wherein the re-wetted oxamide granules are aged at a temperature of 5° C. to 180° C. for 1 to 60 minutes.

13. The process as claimed in claim 10, wherein the redrying step is carried out at a temperature of 100° C. or more.

14. The process as claimed in claim 10, wherein in the re-drying step, water is removed at a rate of 0.5 to 30 g/kg/min.

* * * * *